(12) United States Patent
Feng et al.

(10) Patent No.: US 6,232,344 B1
(45) Date of Patent: May 15, 2001

(54) 13-OXA PROSTAGLANDINS FOR THE TREATMENT OF GLAUCOMA AND OCULAR HYPERTENSION

(75) Inventors: Zixia Feng; Mark R. Hellberg, both of Arlington, TX (US)

(73) Assignee: Alcon Laboratories, Inc., Fort Worth, TX (US)

(*) Notice: Subject to any disclaimer, the term of this patent is extended or adjusted under 35 U.S.C. 154(b) by 0 days.

(21) Appl. No.: 09/308,610
(22) PCT Filed: Dec. 4, 1998
(86) PCT No.: PCT/US98/25681
 § 371 Date: May 21, 1999
 § 102(e) Date: May 21, 1999
(87) PCT Pub. No.: WO99/32441
 PCT Pub. Date: Jul. 1, 1999

Related U.S. Application Data
(60) Provisional application No. 60/068,461, filed on Dec. 22, 1997.

(51) Int. Cl.$^7$ .................. A61K 31/557; C07C 405/00
(52) U.S. Cl. ................ 514/530; 514/570; 514/573; 560/53; 560/60; 560/118; 562/463; 562/470; 562/500
(58) Field of Search ................. 560/53, 60, 118; 562/463, 470, 500; 514/530, 570, 573

(56) References Cited

U.S. PATENT DOCUMENTS

| | | |
|---|---|---|
| 4,599,353 | 7/1986 | Bito . |
| 4,851,523 * | 7/1989 | Collington .................. 560/53 |
| 5,093,329 | 3/1992 | Woodward . |
| 5,321,128 | 6/1994 | Stjernschantz et al. . |

FOREIGN PATENT DOCUMENTS

| | | |
|---|---|---|
| 3613573 A1 | 10/1986 | (DE) . |
| 0160495 A2 | 11/1985 | (EP) . |
| 0265248 A2 | 4/1988 | (EP) . |
| 0561073 A1 | 9/1993 | (EP) . |
| 4229050 A1 | 3/1994 | (EP) . |
| WO 97/23223 | 7/1997 | (WO) . |

OTHER PUBLICATIONS

Thierauch, Prostaglandins and their Receptors: II. Receptor Structure and Signal Transduction, *Journal of Hypertension*, 12:1–5 (1994).

Waterbury, et al., EP$_3$ but not EP$_2$ FP or TP Prostanoid–Receptor Stimulation May Reduce Intraocular Pressure, *Investigative Ophthalmology and Visual Science*, 31(12):2560–2567 (1990).

Woodward, et al., Molecular Characterization and Ocular Hypotensive Properties of the Prostaglandin EP2 Receptor *Journal of Ocular Pharmacology and Therapeutics*, 11(3):447–454 (1995).

Alm, The Potential of Prostaglandin Derivatives in Glaucoma Therapy, *Current Opinion in Ophthalmology*, 4(11):44–50 (1993).

Bito et al., The Ocular Effects of Prostaglandins and the Therapeutic Potential of A New PGF$_{2\alpha}$Analog, PhXA41 (latanoprost), for Glaucoma Management, *J. of Lipid Mediators*, 6:535–543 (1993).

Flach et al., Topical Prostaglandin E$_2$ Effects on Normal Human Intraocular Pressure *Journal of Ocular Pharmacology*, 4(1):13–18 (1988).

Giuffre, The Effects of Prostaglandin F$_{2\alpha}$the Human Eye, *Graefe's Archive Ophthalmology*, 222:139–141 (1985).

Ichikawa et al., Molecular Aspects of the Structures and Functions of the Prostaglandin E Receptors, *J. Lipid Mediators Cell Signaling*, 14:83–87 (1996).

Kerstetter et al., Prostaglandin F$_{2\alpha}$–1–Isopropylester Lowers Intraocular Pressure Without Decreasing Aqueous Humor Flow, *American Journal of Ophthalmology*, 105:30–34 (1988).

Mjalli et al., Synthesis of Some 13–Oxaprostaglandoids, *J. Chem. Soc. Perkin Trans I*, 2105–2109 (1989).

Nakajima, Effects of Prostaglandin D$_2$ and its analogue, BW245C, on Intraocular Pressure in Humans, *Graefe's Archive Ophthalmology*, 229:411–413 (1991).

New research Drug DLO/8149, Drug License Opportunities (IMSWORLD Publications) (June 25, 1990).

\* cited by examiner

Primary Examiner—Robert Gerstl
(74) *Attorney, Agent, or Firm*—Barry L. Copeland

(57) ABSTRACT

13-Oxa analogs of certain prostaglandins and methods of their use in treating glaucoma and ocular hypertension are disclosed.

28 Claims, No Drawings

13-OXA PROSTAGLANDINS FOR THE TREATMENT OF GLAUCOMA AND OCULAR HYPERTENSION

This application claims benefit of Provisional Appln 60/068,461 filed Dec. 22, 1997.

BACKGROUND OF THE INVENTION

The present invention relates to novel compounds and methods for the treatment of glaucoma and ocular hypertension. In particular, the present invention relates to the use of certain 13-oxa analogs of F, D, and E series prostaglandins to treat glaucoma and ocular hypertension.

Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects such as nausea, dyspepsia, fatigue, and metabolic acidosis, which side effects can affect patient compliance and/or necessitate the termination of treatment. Another type of drug, beta-blockers, have increasingly become associated with serious pulmonary side effects attributable to their effects on beta-2 receptors in pulmonary tissue. Sympathomimetics, on the other hand, may cause tachycardia, arrhythmia and hypertension. Recently, certain prostaglandins and prostaglandin derivatives have been described in the art as being useful in reducing intraocular pressure. Typically, however, prostaglandin therapy for the treatment of elevated intraocular pressure is attended by undesirable side-effects, such as irritation and hyperemia of varying severity and duration. There is therefore a continuing need for therapies which control elevated intraocular pressure associated with glaucoma without the degree of undesirable side-effects attendant to most conventional therapies.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F,G,I and J-Series prostaglandins (EP 0 561 073 A1). Of interest in the present invention are compounds which are believed to exhibit IOP lowering mechanisms similar to those exhibited by $PGD_2$ (a D-series prostaglandin), $PGF_{2\alpha}$ (an F-series prostaglandin), and $PGE_2$ (an E-series prostaglandin):

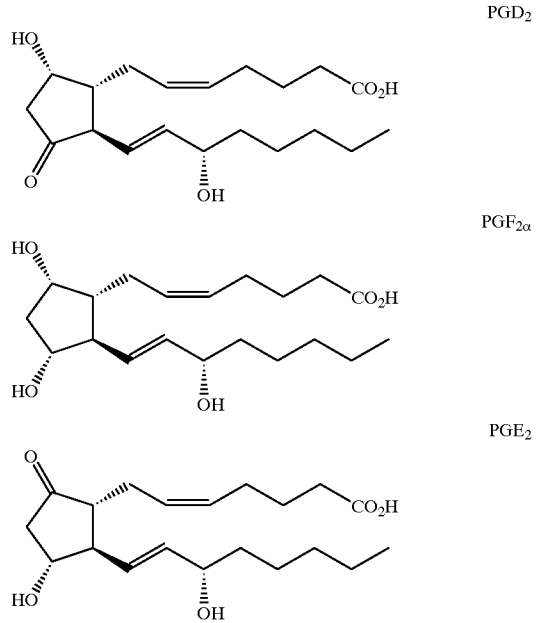

The relationship between $PGD_2$ receptor activation and IOP lowering effects is not well understood. Various publications have reported that $PGD_2$ receptor activation leads to second messenger activation and in particular, to the stimulation of adenylate cyclase and resultant increases in cAMP levels (Thierauch, *Prostaglandins and their Receptors: II. Receptor Structure and Signal Transduction*, Journal of Hypertension, 12:1–5 (1994). Regardless of the mechanism, $PGD_2$ has been shown to lower IOP (Nakajima, *Effects of Prostaglandin $D_2$ and its analogue, BW245C, on Intraocular Pressure in Humans*, Graefe's Archive Ophthalmology, 229:411–413 (1991)). Thus, it has been of interest in the ophthalmic field to develop synthetic $PGD_2$ analogs with IOP lowering efficacy.

Synthetic $PGD_2$-type analogs have been pursued in the art (Nakajima, Goh, Azuma, and Hayaishi, *Effects of prostaglandin D2 and its analogue, BW245C, on intraocular pressure in humans*, Graefe's Archive Ophthalmology, 229:411–413 (1991)). Though $PGD_2$-type molecules lower IOP, these types of molecules have also been associated with undesirable side effects resulting from topical ophthalmic dosing. Such effects have included an initial increase in IOP, conjunctival hyperemia, increases in microvascular permeability, and increases in eosinophile infiltration (Alm, *The Potential of Prostaglandin Derivatives in Glaucoma Therapy*, Current Opinion in Ophthalmology, 4(11):44–50 (1993)).

Similarly, the relationship of $PGF_{2\alpha}$ receptor activation and IOP lowering effects is not well understood. It is believed that $PGF_{2\alpha}$ receptor activation leads to increased outflow of aqueous humor. Regardless of the mechanism, $PGF_{2\alpha}$ and certain of its analogs have been shown to lower IOP (Giuffre, *The Effects of Prostaglandin $F_{2\alpha}$ the Human Eye*, Graefe's Archive Ophthalmology, 222:139–141 (1985); and Kerstetter et al., *Prostaglandin $F_{2\alpha}$-1-Isopropylester Lowers Intraocular Pressure Without Decreasing Aqueous Humor Flow*, American Journal of Ophthalmology, 105:30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (*Graefe's Archive Ophthalmology*, 229:411–413 (1991)).

Though PGF$_{2\alpha}$-type molecules lower IOP, a number of these types of molecules have also been associated with undesirable side effects resulting from topical ophthalmic dosing. Such effects include an initial increase in IOP, breakdown of the blood aqueous barrier and conjunctival hyperemia (Alm, *The Potential of Prostaglandin Derivatives in Glaucoma Therapy, Current Opinion in Ophthalmology*, (11):44–50 (1993)).

The relationship between EP receptor activation and IOP lowering effects is also not well understood. There are currently four recognized subtypes of the EP receptor: (EP$_1$, EP$_2$, EP$_3$, and EP$_4$ (Ichikawa, Sugimoto, Negishi,*Molecular aspects of the structures and functions of the prostaglandin E receptors, J. Lipid Mediators Cell Signaling*, 14:83–87 (1996)). It is known in the art that ligands capable of EP$_2$ receptor activation, such as PGE$_2$ and synthetic analogs (Fallach, Eliason, *Topical Prostaglandin E$_2$ Effects on Normal Human Intraocular Pressure Journal of Ocular Pharmacology*, 4(1):13–18 (1988); Woodward, et al., *Molecular Characterization and Ocular Hypotensive Properties of the Prostaglandin EP2 Receptor Journal of Ocular Pharmacology and Therapeutics*, 11(3):447–454 (1995)), or EP$_3$ receptor activation (Woodward, et al., *Intraocular pressure effects of selective prostanoid receptor agonists involve different receptor subtypes according to radioligand binding studies, Journal of Lipid Mediators*, 6:545–553 (1993); Waterbury, et al., *EP$_3$ but not EP$_2$ FP or TP Prostanoid-Receptor Stimulation May Reduce Intraocular Pressure, Investigative Ophthalmology and Visual Science*, 31(12):2560–2567 (1990)) lower IOP. However, some of these molecules have also been associated with undesirable side effects resulting from topical ophthalmic dosing, including an initial increase in IOP, photophobia, and eye ache (see, for example, Fallach, Eliason, *Topical Prostaglandin E$_2$ Effects on Normal Human Intraocular Pressure, Journal of Ocular Pharmacology*, 4(1):13–18 (1988)).

Based on the foregoing, a need exists for the development of molecules that may activate the PGD$_2$, PGF$_{2\alpha}$, and/or PGE receptors, yielding a more efficacious lowering of IOP, while exhibiting fewer or reduced side effects.

An agent which exhibits comparable or improved efficacy, but with reduced side effects when compared to other agents, is said to have an improved therapeutic profile. It is an object of this invention to provide a class of IOP lowering agents with an improved therapeutic profile over PGF$_{2\alpha}$, PGD$_2$, and PGE$_2$ and methods of their use. It has now been discovered that the presently claimed 13-oxa analogs of prostaglandins meet this objective. 13-oxa analogs of prostaglandins have been reported in the literature (Collington, EP 0160495 A2, (1985); Mjalli, Roberts, *Synthesis of Some 13-Oxaprostaglandoids, J. Chem. Soc. Perkin Trans I*, 2105–2109 (1989)). The presently claimed compounds, however, and their use in IOP lowering are neither disclosed nor suggested in that art.

SUMMARY OF THE INVENTION

The present invention is directed to novel compounds and compositions, and methods of their use in treating glaucoma and ocular hypertension. In particular, the present invention provides certain classes of 13-oxa prostaglandins that may have functional PGF$_{2\alpha}$, PGD$_2$, or PGE receptor agonist activity, and methods of their use in treating glaucoma and ocular hypertension.

DETAILED DESCRIPTION OF THE INVENTION

It has been found that 13-oxa prostaglandin analogs of the present invention exhibit an improved therapeutic profile in the treatment of glaucoma and ocular hypertension when compared to natural prostaglandins and many of their known analogs. The 13-oxa prostaglandin analogs of the present invention have the following formula I:

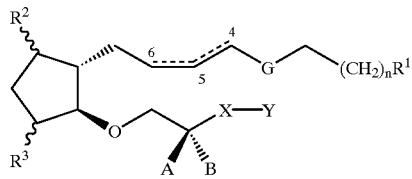

I wherein:
R$^1$=CO$_2$R, CONR$^4$R$^5$, CH$_2$OR$^6$, or CH$_2$NR$^7$R$^8$; where:
   R=H or cationic salt moiety, or CO$_2$R forms a pharmaceutically acceptable ester moiety;
   R$^4$, R$^5$=same or different=H or alkyl; R$^6$=H, acyl, or alkyl;
   R$^7$, R$^8$=same or different=H, acyl, or alkyl; with the proviso that if one of R$^7$, R$^8$=acyl, then the other=H or alkyl;
n=0 or 2;
G=CH$_2$ or O;
R$^2$, R$^3$=same or different=OH, acyloxy, alkoxy, carbonyl, halogen, H, with the proviso that at least one of R$^2$, R$^3$=OH, acyloxy, alkoxy, or carbonyl;

----- = single or non-cumulated double bond;

one of A, B=H, the other=halo, OH, acyloxy, or alkoxy; or A—B=O(CH$_2$)$_2$O or double bonded O;
X=(CH$_2$)$_q$ or (CH$_2$)$_q$ O; where q=1–6; and
Y=a phenyl ring optionally substituted with alkyl, halo, trihalomethyl, alkoxy, acyl, acyloxy, amino, alkylamino, acylamino, or hydroxy; or
X—Y=(CH$_2$)$_p$Y$^1$; where p=0–6; and

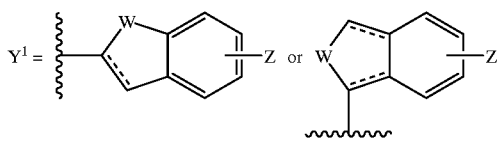

wherein:
   W=CH$_2$, O, S(O)$_m$, NR$^9$, CH$_2$CH$_2$, CH=CH, CH$_2$O, CH$_2$S(O)$_m$, CH=N, or CH$_2$NR$^9$; where m=0–2, and R$^9$=H, alkyl, or acyl;
   Z=H, alkyl, alkoxy, acyl, acyloxy, halo, trihalomethyl, amino, alkylamino, acylamino, or hydroxy; and ----- = single or double bond, or X—Y=cyclohexyl or cyclopentyl.

For purposes of the foregoing and following definitions, the term "pharmaceutically acceptable ester" means any ester that would be suitable for therapeutic administration to a patient by any conventional means without significant deleterious health consequences; and "ophthalmically acceptable ester" means any pharmaceutically acceptable ester that would be suitable for ophthalmic application, i.e.

non-toxic and non-irritating. Preferred are alkyl esters. Most preferred are $C_2$–$C_4$ alkyl esters, and especially isopropyl esters.

Preferred compounds of the present invention are those of formula I above, wherein:

$R^1$=$CO_2R$, where R═H or alkyl;

n=0;

G=$CH_2$;

$R^2$=$R^3$=OH in the α configuration, or $R^2$=O (i.e. a carbonyl) and $R^3$=OH in the α configuration or H;

----- = single or non-cumulated double bond, with the proviso that a double bond between carbons 4 and 5 may not be of the trans configuration;

one of A, B=H, the other=halo or OH;

X=$(CH_2)_2$ or $CH_2O$

Y=phenyl, optionally substituted with halo or trihalomethyl; or

X—Y=$Y^1$; where

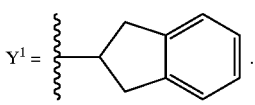

Other preferred compounds of the present invention are those of formula I above, wherein:

$R^1$=$CO_2R$, where R=H or alkyl;

n=0;

G=O;

$R^2$=Cl in the β configuration, and $R^3$=OH in the α configuration;

----- = single or double bond, with the proviso that a single bond exists between carbons 4 and 5;

one of A, B=H, the other=halo or OH;

X—Y=cyclohexyl.

Examples of the most preferred compounds are the following:

| Compound Number | Compound Name | Compound Structure |
|---|---|---|
| II | (5Z)-(9S,11R,15R)-13-oxa-16-(3-chloro-phenoxy)-9,11,15-trihydroxy-17,18,19,20-tetranor-5-prostadienoic acid | 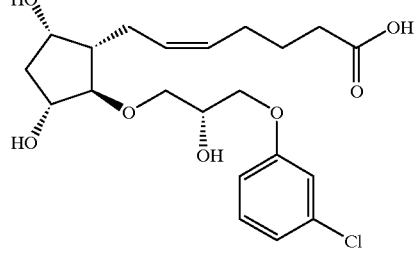 |
| III | (5Z)-(9S,11R,15S)-13-oxa-17-(3-trifluoromethyl-phenyl)-9,11,15-trihydroxy-18,19,20-trinor-5-prostadienoic acid isopropyl ester | 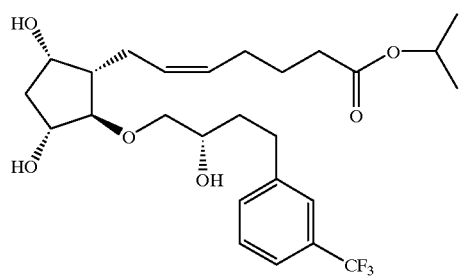 |
| IV | (5Z)-(11R,15R)-9-keto-13-oxa-16-phenoxy-9,11,15-trihydroxy-17,18,19,20-tetranor-5-prostadienoic acid isopropyl ester | 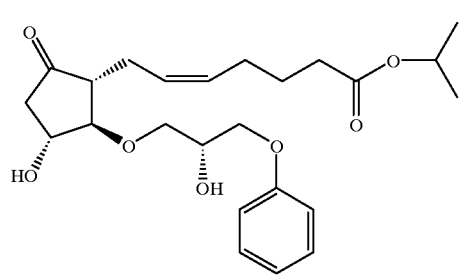 |

| Compound Number | Compound Name | Compound Structure |
|---|---|---|
| V | (5Z)-(9R,11R,15S)-9-chloro-13-oxa-15-cyclohexyl-11,15-dihydroxy-3-oxa-16,17,18,19,20-pentanor-5-prostenoic acid isopropyl ester | 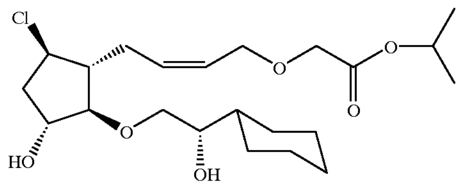 |
| VI | (5Z)-(9S,11R,15R)-13-oxa-17-(3-trifluoromethyl-phenyl)-9,11,15-trihydroxy-18,19,20-trinor-5-prostadienoic acid isopropyl ester | 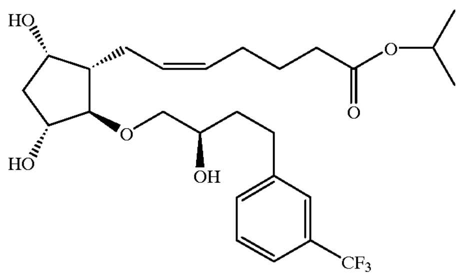 |

Included within the scope of the present invention are the individual enantiomers of the title compounds, as well as their racemic and non-racemic mixtures. The individual enantiomers can be produced by any one of a number of methods, e.g., by purification of a racemic sample by chiral HPLC (*A Practical Guide to Chiral Separations by HPLC*, G. Subramanian, Ed., VCH Publishers: New York, 1994; *Chiral Separations by HPLC*, A. M. Krstulovic, Ed., Ellis Horwood Ltd. Publishers, 1989), or by enantioselective hydrolysis of a racemic carboxylic acid ester by an enzyme (Ohno, M.; Otsuka, M. *Organic Reactions,* 37:1 (1989).

In the following Examples 1–3, the following standard abbreviations are used: g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

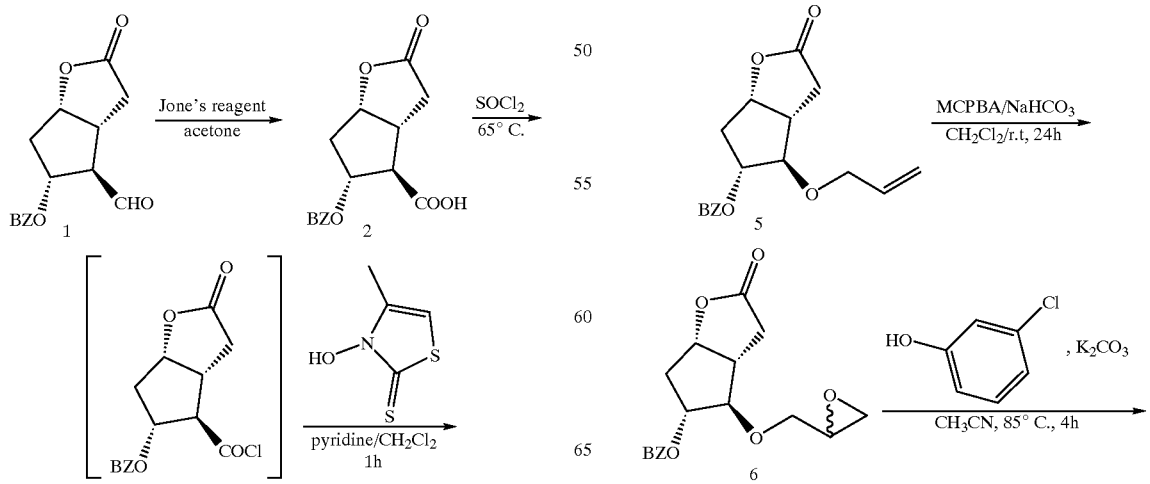

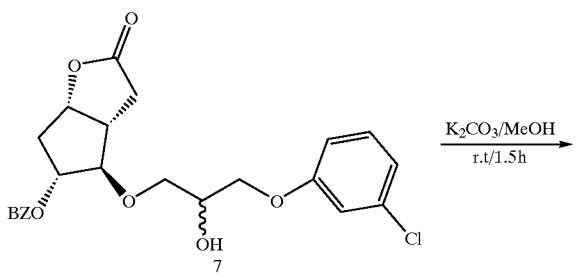

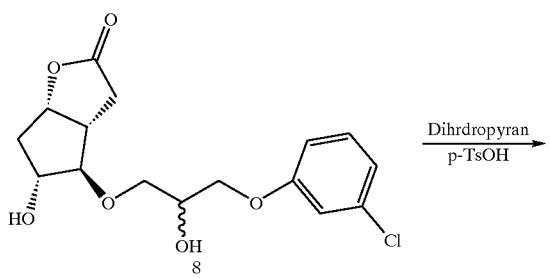

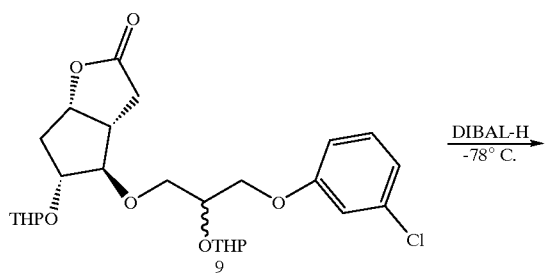

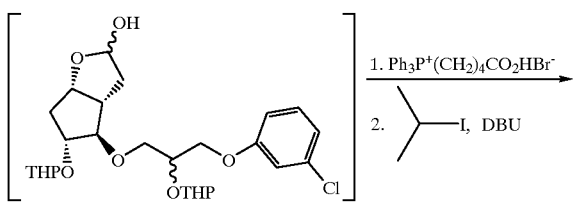

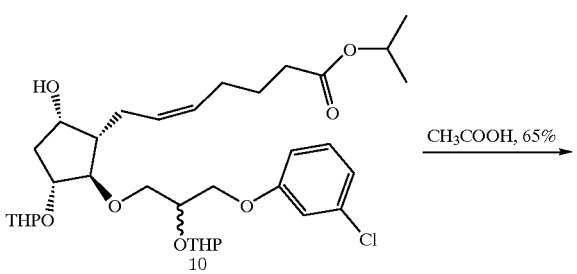

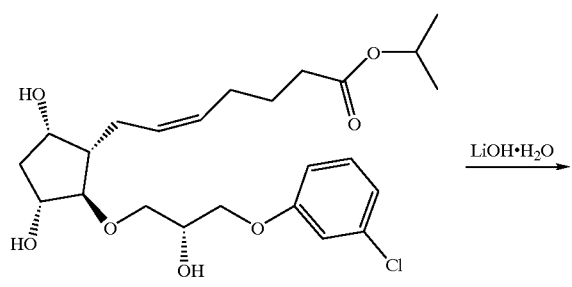

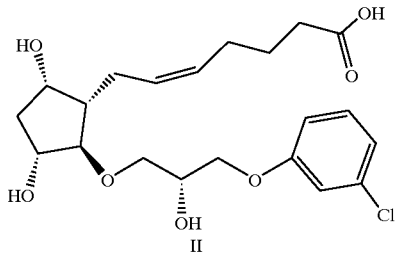

II 6-exo-Carboxylicacid-7-endo-benzoyloxy-2-oxabicyclo[3.3.0]octan-3-one (2)

Corey aldehyde benzoate (15 g, 54.7 mmol) was dissolved in 150 ml of acetone and cooled to 0° C. Jone's reagent was added dropwise with stirring until the brown color did not change to green (25 ml). The mixture was stirred at 0° C. for another 15 min. Isopropanol (30 ml) was added to the reaction mixture. The resulting mixture was filtered through a celite funnel and the filtrate was concentrated. The residue was dissolved in ethyl acetate and washed with water, saturated NaCl, dried over $MgSO_4$, filtered and concentrated. The residue was crystallized in ethyl acetate and hexane (5:1). White crystals of 2 (13.4 g) were obtained. MS, m/z calcd. for $C_{15}H_{15}O_6$ [(M+H)$^+$], 291; found, 291.

7-α-Benzoyloxy-cis-oxabicyclo[3.3.0]octan-3-one-6β-carboxy-4-methylthiazole-2(3H)-thion (3)

Compound 2 (10 g, 34.47 mmol) in 50 ml of thionyl chloride was gently refluxed is for 3 h and then concentrated to a residue. It was dissolved in 30 ml of $CH_2Cl_2$ and then added to a solution of 3-hydroxy-4-methylthiazole-2(3H)-thione (3.56 g, 24.1 mmol) in 30 ml of $CH_2Cl_2$ in dry pyridine (4.2 ml, 51.7 mmol). The resulting mixture was stirred at room temperature for 1 h. The solvent was evaporated and the residue was put in a solution comprised of 300 ml of ethyl acetate and 100 ml of hexane. The white crystals formed were washed with ethyl acetate and hexane (3:1) and dried in vacuum to yield 3 (10.1 g). MS, m/z calcd. for $C_{19}H_{18}O_6NS_2$ [(M+H)$^+$], 420; found: 420.

6β-Hydroxy-7α-benzoyloxy-cis-2-oxabicyclo[3.3.0]octan-3-one (4)

Antimony triphenylsulphide (2 g, 4.45 mmol) was added to a solution of 3 (0.97, g, 2.23 mmol) in 8 ml of $CH_2Cl_2$. The mixture was stirred in an open flask at room temperature for 16 h. The white solid was filtered and the solution was evaporated to dryness. Purification of the residue by flash chromatography using ethyl acetate and hexane (1:1) afforded the desired nor-alcohol 4 (0.4 g). $^1$H NMR (CDCl$_3$) δ 7.99–7.95 (m, 2H ), 7.62–7.54 (m, 1H ), 7.48–7.27 (m, 2H ), 5.32–5.20 (m, 2H ), 4.25 (s, 1H), 3.06–2.36(m, 6 H). $^{13}$C NMR (CDCl$_3$) δ 176.6 (C), 166.5 (C), 113.6 (CH), 129.7 (CH), 128.7 (C), 128.6 (CH), 84.1 (CH), 81.9 (CH), 81.1 (CH), 45.7 (CH), 36.4 (CH$_2$), 33.5 (CH$_2$). MS, m/z calcd. for $C_{14}H_{15}O_5$ (M+H)$^+$263; found: 263.

6β-Allyloxy-7α-benzoyloxy-cis-2-oxabicyclo[3.3.0]octan-3-one (5)

Compound 4 (0.4 g, 1.53 mmol), allyl bromide (1 ml, 12.2 mmol) and silver(I) oxide (1.1 g, 4.6 mmol) were stirred in 8 ml of dry DMF at room temperature for 48 h. Water (2 ml) was added and the mixture was filtered through a celite coated funnel, and washed with ethyl acetate. The filtrate was extracted with ethyl acetate. The combined organic extracts were washed with a saturated NaCl solution and dried over anhydrous MgSO$_4$ Concentration of the combined extracts under reduced pressure, and chromatography of the residue on silica gel, eluting with 40% ethyl acetate in hexane, gave 0.36 g of 5 as a light yellow oil. $^1$H NMR (CDCl$_3$) δ 8.01–7.95 (m, 2H), 7.61–7.54 (m, 1H), 7.48–7.41 (m, 2H), 6.00–5.80 (m, 1H), 5.50–5.14 (m, 4H), 4.25–4.15 (m, 1H), 3.12–2.86(m, 4H), 2.56–2.36 (m, 3H); $^{13}$C NMR (CDCl$_3$) δ 176.7 (C), 165.7 (C) 133.9 (CH), 133.5 (CH), 129.7 (CH), 129.6 (C), 128.6 (CH), 117.7 (C), 88.7 (CH), 84.8 (CH), 77.9 (CH), 70.7 (CH$_2$), 44.5 (CH), 36.5 (CH$_2$), 33.7 (CH$_2$). MS, m/z calcd. for C$_{17}$H$_{19}$O$_5$Na (M+Na)$^+$ 325; found: 325.

6β-Glycidoxy-7α-benzoyloxy-cis-2-oxabicyclo[3.3.0]octan-3-one (6)

The allyl ether 5 (0.36 g, 1.19 mmol) was stirred with m-chloroperoxybenzoic acid (0.62 g, 3.56 mmol) and sodium hydrogen carbonate (0.36 g, 4.3 mmol) in 10 ml of CH$_2$Cl$_2$ at 0° C. The mixture was warmed slowly to room temperature and stirred for 24 h. The reaction mixture was washed with saturated aqueous sodium sulphite, saturated sodium hydrogen carbonate, water and brine, and dried over anhydrous MgSO$_4$. Evaporation of solvent afforded the crude product, which was chromatographed on a silica gel column, eluting with 60% ethyl acetate in hexanes, to provide the title compound 6 as an oil 0.12 g. $^1$H NMR (CDCl$_3$) δ 7.99–7.94 (m, 2H), 7.61–7.54 (m, 1H), 7.48–7.40 (m, 2H), 5.48 (s, 1H), 5.27–5.22 (m, 1H), 4.10–3.91(m, 2H), 3.64–3.46 (1H), 3.17–2.80 (m, 4 H), 2.68–2.42 (m, 4H); $^{13}$C NMR (CDCl$_3$) δ 176.5 (C), 165.7 (C), 133.5 (CH), 129.7 (CH), 129.6 (C), 128.5 (CH), 89.7 (CH), 84.6 (CH), 77.7 (CH), 71.0 (CH$_2$), 70.2 (CH$_2$), 50.6 (CH), 44.3 (CH), 44.1 (CH$_2$), 36.8(CH$_2$), 33.6 (CH2). MS, m/z calcd. for C$_{17}$H$_{19}$O$_6$ (M+H)$^+$ 340; found: 340.

6β-[2αβ-Hydroxy-3-(3-chloro)phenoxy-propoxy]-7α-benzoyloxy-cis-2-oxabicyclo[3.3.0]octan-3-one (7)

To a solution of 6 (0.1 g, 0.314 mmol) in 2 ml of acetonitrile, 3-chlorophenol (0.07 ml, 0.63 mmol) and potassium carbonate (0.13 g, 0.95 mmol) were added and the mixture was refluxed for 4 h. After cooling, the mixture was filtered and the filtrate was concentrated. The residue was chromatographed on a silica gel column eluting with ethyl acetate-hexanes (1:1) to provide the title compound 7 as a yellowish oil 0.09 g. $^1$H NMR (CDCl$_3$ ) δ 7.98–7.94 (m, 2H), 7.57–7.44 (m, 3H), 7.25–6.79 (m, 4H), 5.50 (s, 1H), 5.25–5.23 (m, 1H), 4.14–3.77 (m, 4H), 3.06–2.01(m, 6 H). $^{13}$C NMR (CDCl$_3$) δ 176.5 (C), 165.8 (C), 159.1 (C), 135.0 (C), 113.6 (CH), 130.0 (C), 129.7 (CH), 129.0 (C), 128.7 (CH), 121.5 (CH), 115.0 (CH), 113.1 (CH), 90.1 (CH), 84.7 (CH), 77.7 (CH), 70.7 (CH$_2$), 69.0 (CH), 68.8 (CH$_2$), 44.3 (CH), 36.8 (CH$_2$), 33.7 (CH$_2$). MS, m/z calcd. for C$_{23}$H$_{23}$O$_7$ClNa (M+Na)$^+$ 469; found: 469.

6β-[2αβ-Hydroxy-3-(3-chloro)phenoxy-propoxy]-7α-hydroxy-cis-2-oxabicyclo[3.3.0]octan-3-one (8)

Potassium carbonate(0.03 g, 0.2 mmol) was added to a solution of 7 (0.09 g, 0.2 mmol) in 2 ml of methanol. The resulting mixture was stirred at room temperature for 1.5 h. Ethyl acetate (2 ml) and 1N HCl(1 ml) were added. The aqueous layer was separated and extracted with ethyl acetate (3×3 ml). The combined organic extracts were washed with saturated NaHCO$_3$ and saturated NaCl solutions and dried over anhydrous MgSO$_4$. Evaporation of solvent afforded crude product which was chromatographed on silica gel (ethyl acetate-hexanes, 5:1) to provide the title compound 8 as a yellowish oil 0.075 g. MS, m/z calcd. for C$_{16}$H$_{19}$O$_6$ClNa(M+Na)$^+$ 365; found: 365

6β-[2αβ-tetrahydro-2H-pyran-2-yl)oxy-3-(3-chloro) phenoxy-propoxy-7α-tetrahydro-2H-pyran-2-yl)oxy-cis-2-oxabicyclo[3.3.0]octan-3-one (9)

3, 4-Dihydro-2H-pyran (0.08 ml, 0.85 mmol) was added to a solution of 8 (0.075 g, 0.211 mmol) in CH$_2$Cl$_2$ (1 ml) and the mixture was cooled to 0° C. p-Toluenesulfonic acid monohydrate (2 mg, 0.01 mmol) was added and the resulting mixture was stirred at 0° C. for 30 min and then quenched by addition of saturated NaHCO$_3$ (1 ml). The aqueous layer was separated and extracted with CH$_2$Cl$_2$ (3×3 ml). The combined organic extracts were washed with a saturated NaCl solution and dried over anhydrous MgSO$_4$. Evaporation of solvent afforded the crude product which was chromatographed on silica gel (ethyl acetate-hexanes, 1:2) to provide the title compound 9 as an oil 0.1 g. MS, m/z calcd. for C$_{26}$H$_{35}$O$_8$ClNa(M+Na)$^+$ 533; found: 533.

5Z-(9S,11R,15RS)-13-oxa-16-(3-chloro)phenoxy-propoxyl-9-hydroxy-11,15-bis (tetrahydro-2H-pyran-2-yl)oxy-17,18,19,20-tetranor-5-prostadienoic acid isopropyl ester (10)

To a solution of 9 (0.1 g, 0.2 mmol) in 1 ml of toluene at −78° C., was added dropwise a 1.5M solution of DIBAL-H in toluene (0.18 ml, 0.26 mmol). The resulting mixture was stirred at −78° C. for 1 h. Methanol (0.5 ml) was added to quench the reaction. Saturated ammonium chloride (2 ml) and ethyl acetate (3 ml) were added, the mixture was extracted with ethyl acetate (3×3 ml). The combined organic extracts were washed with a saturated NaCl solution and dried over anhydrous MgSO$_4$, filtered and concentrated to a white form (0.1 g), which was used for next step without further purification.

To a suspension of (4-carboxybutyl) triphenylphosphonium bromide (0.22 g, 0.5 mmol) in THF (1 mL) at 0° C. (bath temperature) was added a 1 M solution of potassium tert-butoxide in THF (1 ml, 1 mmol). After 40 min, a solution of the crude product above (0.1 g, 0.2 mmol) in THF (2 ml) was added dropwise under N$_2$, and the reaction was stirred at room temperature for 1 h. Saturated ammonium chloride (2 ml) and ethyl acetate (3 ml) were added. The aqueous layer was treated with 2N HCl to adjust the pH to 5 and was then extracted with ethyl acetate (3×3 ml). The combined organic layer was washed with a saturated NaCl solution, dried over anhydrous MgSO$_4$, filtered and concentrated to a white form. This was dissolved in acetone (2 ml), the solution was cooled to 0° C. (bath temperature), and DBU (0.2 ml, 1.2 mmol) was added. After 20, min isopropyl iodide was added (0.1 ml, 1.0 mmol) and the reaction was warmed to room temperature and stirred overnight. Saturated ammonium chloride (2 ml) and ethyl acetate (3 ml) were added, the mixture was extracted with ethyl acetate (3×3 ml). The combined organic extracts were washed with a saturated NaCl solution, dried over anhydrous MgSO$_4$, filtered and concentrated to a colorless oil, which was chromatographed on a silica gel column, eluting with 30% ethyl acetate in hexane, to afford 10 (0.065 g). MS, m/z calcd. for C$_{34}$H$_{51}$O$_9$ClNa [M+Na]$^+$, 661; found: 661.

5Z-(9S,11R,15R)-13-oxa-16-(3-chloro)phenoxy-propoxy]-9,11,15-trihydroxy-17,18, 19,20-tetranor-5-prostadienoic acid isopropyl ester (11)

Compound 10 (65 mg, 0.1 mmol) was stirred in 1 ml of 65% acetic acid and 1 ml of THF at 55° C. for 1.5 h. The solvent was evaporated and the residue was dried under vacuum. The crude product was chromatographed on a silica gel column eluting with 80% ethyl acetate in hexane and followed by HPLC chiral separation to afford 11 (20 mg). $^1$H NMR of 11 (CDCl$_3$) δ 7.20–7.12 (m, 1H), 7.08–6.85 (m, 2H), 6.75–6.70 (m, 1H), 5.40–5.31 (m, 2H), 4.95–4.89 (m, 1H), 4.13–3.57 (m, 8H), 2.33–1.57 (m, 11H), 1.17–1.14 (d, J=6 Hz, 6H). $^{13}$C NMR (CDCl$_3$) δ 173.6 (C), 159.3 (C), 134.8 (C), 130.2 (CH), 129.9 (CH), 128.9 (CH), 121.2 (CH), 115.0 (CH), 113.0 (CH), 93.04 (CH), 77.1 (CH), 73.4 (CH), 71.3 (CH$_2$), 69.3 (CH), 69.1 (CH$_2$), 67.8 (CH), 51.4 (CH), 41.2 (CH$_2$), 34.0 (CH$_2$), 26.6 (CH$_2$), 25.8 (CH$_2$), 24.9 (CH$_2$), 21.8 (CH$_3$). MS (ESI), m/z calcd. for C$_{24}$H$_{35}$O$_7$Cl [(M+NH$_4$)$^+$], 488; found: 488, [(M+1)$^+$], 471; found, 471.

5Z-(9S,11R,15R)-13-oxa-16-(3-chloro)phenoxy-propoxyl-9,11,15trihydroxy-17,18, 19,20-tetranor-5prostadienoic acid (II)

A mixture of 11 (18 mg, 0.04 mmol), lithium hydroxide monohydrate (17 mg, 0.4 mmol), methanol (1 ml) and water (0.1 ml) was stirred at room temperature overnight. Saturated KH$_2$PO$_4$ was added to adjust the pH to 6 and the mixture was extracted with ethyl acetate (3×3 ml). The combined organic layer was washed with a saturated NaCl solution, dried over anhydrous MgSO$_4$, filtered and concentrated to a colorless oil, which was chromatographed on a short silica gel column, eluting with 5% methanol in ethyl acetate, to afford II (8 mg). $^1$H NMR (CDCl$_3$)) δ 7.25–7.22 (m, 1H), 6.98–6.88 (m, 3H), 5.49–5.47 (m, 1H), 5.34–5.32 (m, 1H), 4.09–4.02 (m, 5H), 3.78–3.77 (d, 1H, J=6 Hz), 3.67–3.65 (d, 1H, J=12 Hz), 3.57–3.55 (d, 1H, J=6 Hz), 2.28–2.23 (m, 5H), 2.10–2.09 (m, 2H), 2.07–2.05 (m, 1H), 1.64–1.61 (m, 3H). $^{13}$C NMR (CDCl$_3$) δ 178.0 (C), 161.3 (C), 135.9 (C), 131.6 (CH), 130.6 (CH), 130.2 (CH), 121.9 (CH), 116.0 (CH), 114.2 (CH), 92.9 (CH), 77.4 (CH), 72.3 (CH$_2$), 71.9 (CH), 70.8 (CH$_2$), 70.3 (CH$_2$), 51.1 (CH), 42.2 (CH$_2$), 27.7 (CH$_2$), 26.4 (CH$_2$), 26.1 (CH$_2$). MS (ESI), m/z calcd. for C$_{21}$H$_{29}$O$_7$Cl [(M+NH$_4$)$^+$], 446; found: 446, [(M+1)$^+$], 429; found: 429.

EXAMPLE2

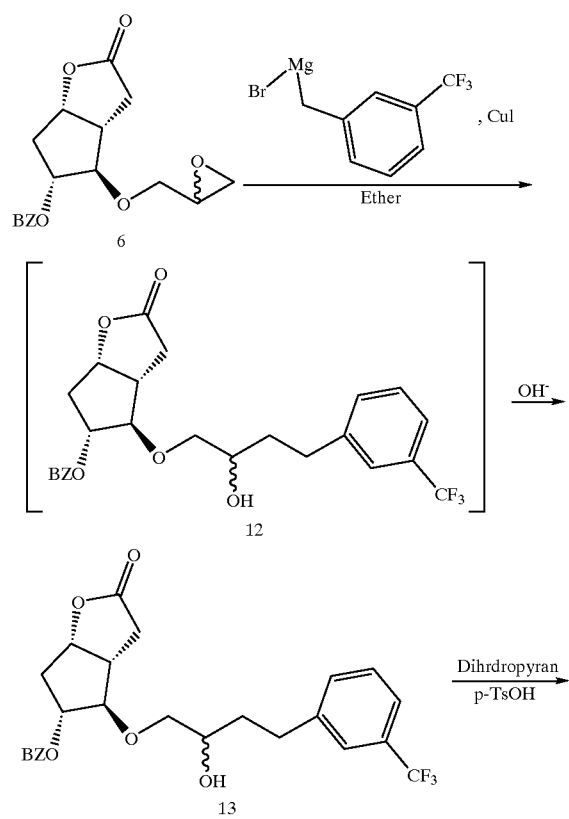

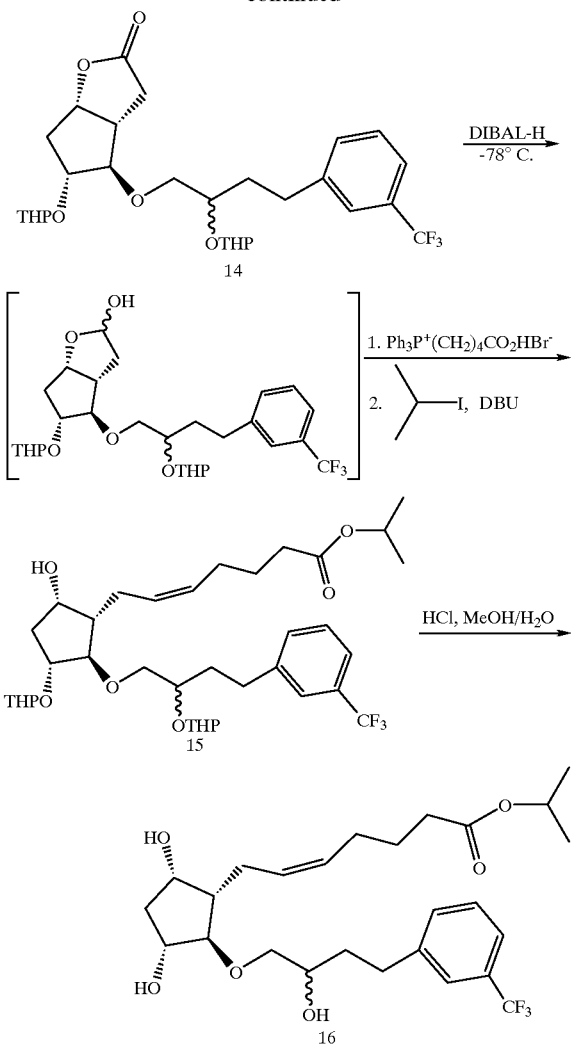

5Z-(9S,11R,15RS)-13-oxa-17-[(3-trifluoromethyl)phenyl]-9,11,15-trihydroxy-18, 19,20-trinor-5-prostadienoic acid isopropyl ester (16)

Copper(I) iodide (1.8 g, 9.4 mmol) was stirred in dry diethyl ether (10 ml) at −30° C. under N$_2$. m-Trifluoromethylbenzylmagnesium bromide (18.8 mmol) in 10 ml of ether was added dropwise and stirred at −30° C. for 15 min. The mixture was cooled to −78° C., and the epoxide 6 (0.5 g, 1.57 mmol) in ether (8 ml) was added dropwise. The resulting mixture was stirred for 6 h, after which saturated ammonium chloride (5 ml) was added and the mixture warmed to room temperature and stirred for 15 min. The two layers were separated and the aqueous layer was extracted with ethyl acetate (3×10 ml). The combined organic extracts were washed with a saturated NaCl solution, dried over anhydrous MgSO$_4$, filtered and concentrated to a colorless oil, which was chromatographed on a silica gel column, eluting with ethyl acetate, to afford 13 (0.11 g). MS, m/z calcd. for C$_{18}$H$_{21}$O$_5$F$_3$Na [M+Na]$^+$, 397; found: 397.

The intermediates 14 and 15 were synthesized using the general methods employed in the synthesis of 9 and 10 described in Example 1.

Compound 15 (55 mg, 0.08 mmol) was stirred in 1 ml of MeOH, 0.1 ml of water and 1 drop of 12N HCl at 0° C. for 15 min, and room temperature for 2 h. 2 ml each of ethyl acetate and saturated NaHCO₃ were added. The two layers were separated and the aqueous layer was extracted with ethyl acetate (3×5 ml). The combined organic extracts were washed with a saturated NaCl solution, dried over anhydrous MgSO₄, filtered and concentrated to an oil residue, which was chromatographed on a silica gel column, eluting with ethyl acetate, to afford 16 (22 mg). ¹H NMR (CDCl₃) δ 7.46–7.38 (m, 4H), 5.46–5.44 (m, 2H ), 5.06–4.94 ( m, 1H ), 4.22–3.62 ( m, 8H ), 2.41–1.68 ( m, 1H), 1.24–1.21 (d, J=6 Hz, 6H). ¹³C NMR (CDCl₃) δ 173.5(C), 142.8(C), 131.9 (CH), 130.0 (CH), 128.7 (CH), 125.1 (CH), 122.8 (CH), 93.2 (CH), 92.7 (CH), 77.2 (CH), 75.8 (CH₂), 74.7 (CH₂), 73.6 (CH), 72.9 (CH), 69.6 (CH), 67.7 (CH), 51.5 (CH), 51.1 (CH), 41.3 (CH₂), 34.0 (CH₂), 31.6 (CH₂), 26.6 (CH₂), 26.2 (CH₂), 24.8(CH₂). 21.8 (CH). MS, m/z calcd. for $C_{26}H_{37}O_6F_3Na$ [(M+Na)⁺], 525; found: 525.

EXAMPLE 3

More compound 16 (0.36 g) was synthesized using the same method described above and followed by HPLC chiral separation to provide III (95 mg) and VI (110 mg). ¹H NMR of III (CDCl₃) δ 7.45–7.27 (m, 4H), 5.48–5.40 (m, 2H), 5.06–4.93 (m, 1H), 4.21–411 (m, 2H), 3.65–3.62 (m, 1H), 3.57–3.50 (m, 3H), 2.37–1.64 (m, 1SH), 1.24–1.21 (d, J=6 Hz, 6H). ¹³C NMR (CDCl₃) δ 173.6 (C), 142.8 (C), 131.9 (CH), 130.3 (C), 129.9 (CH), 128.8 (CH), 125.1 (C), 125.0 (CH), 122.8 (CH), 93.0 (CH), 77.5 (CH), 75.0 (CH₂), 73.8 (CH), 70.0 (CH), 68.1 (CH), 51.8 (CH), 41.6 (CH₂), 34.9 (CH₂), 34.3 (CH₂), 31.9 (CH₂), 26.7 (CH₂), 26.2 (CH₂), 25.2 (CH₂), 22.1 (CH₃). MS (ESI), m/z calcd. for $C_{26}H_{37}O_6F_3$ [M+NH₄]⁺, 520; found: 520, [(M+H)⁺], 503; found: 503.

¹H NMR of VI (CDCl₃) δ 7.45–7.27 (m, 4H), 5.49–5.41 (m, 2H), 5.06–4.94 (m, 1H), 4.23–410 (m, 2H), 3.71–3.56 (m, 3H), 3.42–4.37 (m, 1H), 2.86–1.65 (m, 15H), 1.24–1.21

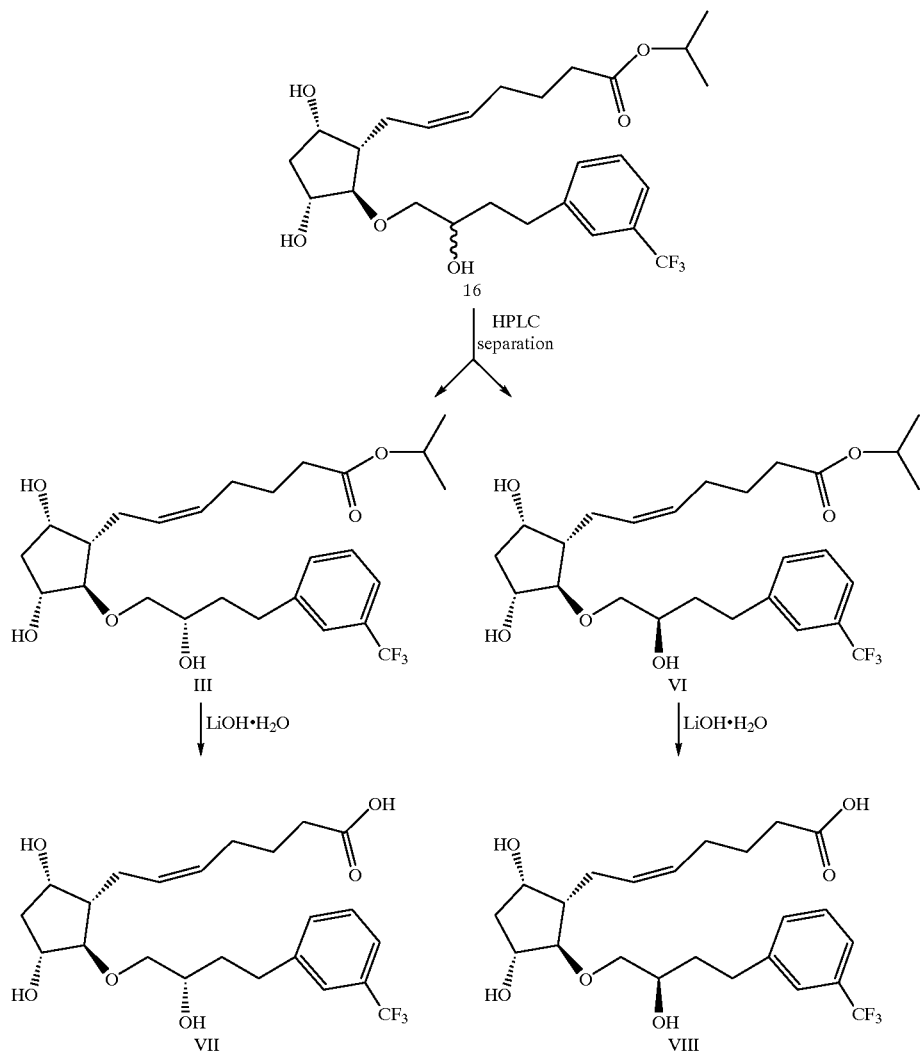

5Z-(9S, 11R, 15S)-13-oxa-17-(3-trifluoromethyl)phenyl-9,11,15-trihydroxy-18, 19,20-trinor-5-prostadienoic acid isopropyl ester (II), and 5Z-(9S,11R,15R)-13-oxa-17-(3-trifluoromethyl)phenyl-9,11,15-trihydroxy-18,19,20-trinor-5-prostadienoic acid isopropyl ester (VI)

(d, J=6 Hz, 6H). ¹³C NMR (CDCl₃) δ 173.6 (C), 142.8 (C), 131.9 (CH), 130.6 (C), 129.9 (CH), 128.8 (CH), 125.5 (C), 125.2 (CH), 122.8 (CH), 93.1 (CH), 77.1 (CH), 74.8 (CH₂), 73.7 (CH), 69.7 (CH), 67.8 (CH), 51.6 (CH), 41.4 (CH₂), 34.5 (CH₂), 34.0 (CH₂), 31.6 (CH₂), 26.6 (CH₂), 25.9

($CH_2$), 24.9 ($CH_2$), 21.8 ($CH_3$). MS (ESI), m/z calcd. for $C_{26}H_{37}O_6F_3$ [$(M+NH_4)^+$], 520; found: 520, [$(M+H)^+$], 503; found: 503.

5Z-(9S, 11R, 15S)-13-oxa-17-(3-trifluoromethyl)phenyl-9, 11,15-trihydroxy-18, 19,20-trinor-5-prostadienoic acid (VII) and 5Z-(9S, 11R, 15R)-13-oxa-17-(3-trifluoromethyl) phenyl-9,11,15-trihydroxy-18, 19,20-trinor-5-prostadienoic acid (VIII)

Compounds VI (12 mg) and VIII (10 mg) were obtained using the same methods described in Example 1. Compound VI: $^1$H NMR ($CD_3OD$) δ 7.51–7.45 (m, 4H), 5.51–5.49 (m, 1H), 5.37–5.35 (m, 1H), 4.09 (s, 1H), 4.0 (s, 1H), 3.66–3.64 (m, 2H), 3.53–3.49 m, 2H), 2.90–2.87 (m, 1H), 2.73–2.70 (m, 1H), 2.29–2.25 (m, 5H), 2.22–2.11 (m, 2H), 1.80–1.74 (m, 3H), 1.65–1.62 (m, 3H). $^{13}$C NMR ($CDCl_3$) δ 177.8 (C), 145.0 (C), 133.4 (CH), 131.8 (C), 130.5 (CH), 130.4 (CH), 130.2 (CH), 126.7 (C), 126.1 (CH), 123.6 (CH), 91.2 (CH), 76.0 (CH), 74.2 ($CH_2$), 70.4 (CH), 69.3 (CH), 49.6 (CH), 47.9 (CH), 40.8 ($CH_2$), 35.1 ($CH_2$), 33.1 ($CH_2$), 31.1 ($CH_2$), 26.3 ($CH_2$), 24.6 ($CH_2$). MS (ESI), m/z calcd. for $C_{23}H_{31}O_6F_3$ [$(M+NH_4)^+$], 478; found: 478, [$(M+H)^+$], 461; found: 461.

Compound VIII: $^1$H NMR ($CD_3OD$) δ 7.51–7.45 (m, 4H), 5.51–5.49 (m, 1H), 5.37–5.35 (m, 1H), 4.09 (s, 1H), 4.0 (s, 1H), 3.69–3.65 (m, 1H), 3.63–3.61 (m, 1H), 3.55–3.53 (m, 1H), 3.49–3.47 (m, 1H), 2.90–2.87 (m, 1H), 2.73–2.70 (m, 1H), 2.31–2.25 (m, 5H), 2.12–2.09 (m, 2H), 1.85–1.83 (m, 1H), 1.73–1.71 (m, 2H), 1.64–1.60 (m, 3H). $^{13}$C NMR ($CDCl_3$) δ 177.8 (C), 145.0 (C), 133.4 (CH), 131.8 (C), 130.5 (CH), 130.4 (CH), 130.2 (CH), 126.7 (C), 126.1 (CH), 123.6 (CH), 91.2 (CH), 76.0 (CH), 74.5 ($CH_2$), 70.4 (CH), 69.3 (CH), 49.6 (CH), 47.9 (CH), 40.8 ($CH_2$), 35.2 ($CH_2$), 33.2 ($CH_2$), 31.1 ($CH_2$), 26.2 ($CH_2$), 24.7 ($CH_2$). MS (ESI), m/z calcd. for $C_{23}H_{31}O_6F_3$ [$(M+NH_4)^+$], 478; found: 478, [$(M+H)^+$], 461; found: 461.

The 13-oxa prostaglandins of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between 4.5 to 8.0, preferably between about 7.0 and 7.5. The compounds are preferably formulated as between about 0.0005 to about 0.07 wt % and, most preferably, between about 0.005 and about 0.05 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents, and viscosity building agents.

Antimicrobial Preservatives:

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents:

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil) cyclodextrin; HCO-40 or other agents known to those skilled in the art. Such co-solvents are typically employed at a level between about 0.01% and about 2% by weight.

Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methyl cellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of the 13-oxa prostaglandins of the present invention include the following Examples 4–7:

EXAMPLE 4

| Ingredient | Amount (wt %) |
| --- | --- |
| Compound III | 0.01 |
| Phosphate Buffered Saline | 1.0 |
| Polysorbate 80 | 0.5 |
| Purified water | q.s. to 100% |

EXAMPLE 5

| Ingredient | Amount (wt %) |
| --- | --- |
| Compound V | 0.005 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| CREMOPHOR ® EL | 0.1 |
| Benzalkonium chloride | 0.01 |
| HCl and/or NaOH | pH 7.3–7.4 |
| Purified water | q.s. to 100% |

EXAMPLE 6

| Ingredient | Amount (wt %) |
| --- | --- |
| Compound IV | 0.05 |
| Phosphate Buffered Saline | 1.0 |
| Hydroxypropyl-β-cyclodextrin | 4.0 |
| Purified water | q.s. to 100% |

EXAMPLE 7

| Ingredient | Amount (wt %) |
| --- | --- |
| Compound VI | 0.01 |
| Phosphate Buffered Saline | 1.0 |
| Polysorbate 80 | 0.5 |
| Purified water | q.s. to 100% |

The invention has been described by reference to certain preferred embodiments; however, it should be understood that it may be embodied in other specific forms or variations thereof (including all genera and species encompassed within the invention) without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma or ocular hypertension in a patient, which comprises administering to the patient a pharmaceutically effective amount of a compound of formula I:

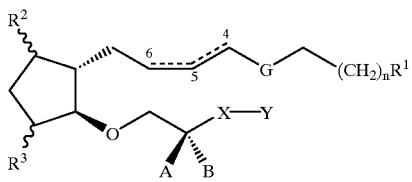

wherein:
$R^1$=$CO_2R$, $CONR^4R^5$, $CH_2OR^6$, or $CH_2NR^7R^8$; where:
R=H or cationic salt moiety, or $CO_2R$ forms a pharmaceutically acceptable ester moiety;
$R^4$, $R^5$=same or different=H or alkyl; $R^6$=H, acyl, or alkyl;
$R^7$, $R^8$=same or different=H, acyl, or alkyl; with the proviso that if one of $R^7$, $R^8$=acyl, then the other=H or alkyl;
n=0 or 2;
G=$CH_2$ or O;
$R^2$, $R^3$=same or different=OH, acyloxy, alkoxy, carbonyl, halogen, H, with the proviso that at least one of $R^2$, $R^3$=OH, acyloxy, alkoxy, or carbonyl;

----- = single or non-cumulated double bond;

one of A, B=H, the other=halo, OH, acyloxy, or alkoxy; or A—B=$O(CH_2)_2O$ or double bonded O;

X=$(CH_2)_q$ or $(CH_2)_qO$; where q=1–6; and
Y=a phenyl ring optionally substituted with alkyl, halo, trihalomethyl, alkoxy, acyl, acyloxy, amino, alkylamino, acylamino, or hydroxy; or
X—Y=$(CH_2)_pY^1$; where p=0–6; and

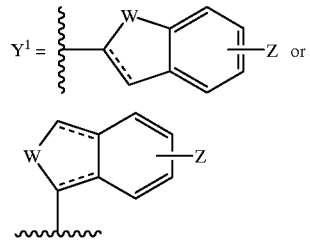

wherein:
W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;
Z=H, alkyl, alkoxy, acyl, acyloxy, halo, trihalomethyl, amino, alkylamino, acylamino, or hydroxy; and ----- = single or double bond, X—Y=cyclohexyl or cyclopentyl.

2. The method of claim 1, wherein the compound is administered topically.

3. The method of claim 2, wherein the compound is administered as a solution, suspension, or emulsion in an ophthalmically acceptable vehicle.

4. The method of claim 2, wherein the concentration of the compounds is between about 0.00003 to about 0.5 weight percent.

5. The method of claim 4, wherein the concentration of the compounds is between about 0.0005 to about 0.03 weight percent.

6. The method of claim 5, wherein the concentration of the compounds is between about 0.005 to about 0.05 weight percent.

7. The method of claim 1, wherein:

$R^1$=$CO_2R$, where R=H or $CO_2R$ forms a pharmaceutically acceptable ester moiety;
n=0;
G=$CH_2$;
$R^2$=$R^3$=OH in the α configuration, or $R^2$=O (as a carbonyl) and $R^3$=OH in the α configuration or H;

----- = single or non-cumulated double bond, with the proviso that a double bond between carbons 4 and 5 may not be of the trans configuration;
one of A, B=H, the other=halo or OH;
X=$(CH_2)_2$ or $CH_2O$; and
Y=phenyl, optionally substituted with halo or trihalomethyl; or X—Y=Y$^1$; where

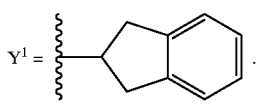

8. The method of claim 7, wherein the compound is:

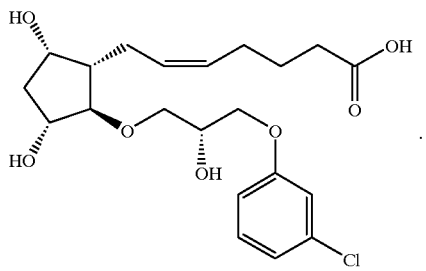

9. The method of claim 7, wherein the compound is:

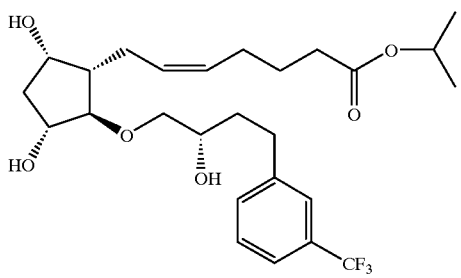

10. The method of claim 7, wherein the compound is:

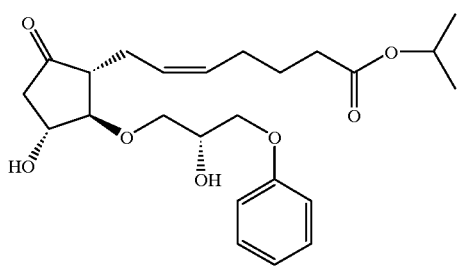

11. The method of claim 7, wherein the compound is:

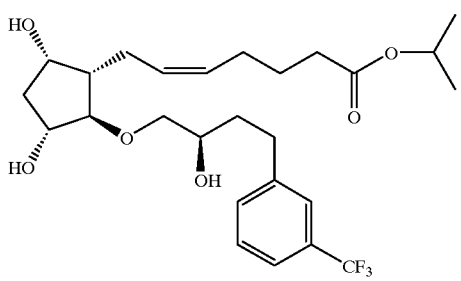

12. The method of claim 1, wherein:
R$^1$=CO$_2$R, where R=H or alkyl;
n=0;
G=O;
R$^2$=Cl in the β configuration, and R$^3$=OH in the α configuration;

----- = single or double bond, with the proviso that a single bond exists between carbons 4 and 5;
one of A, B=H, the other=halo or OH;
X—Y=cyclohexyl.

13. The method of claim 12, wherein the compound is:

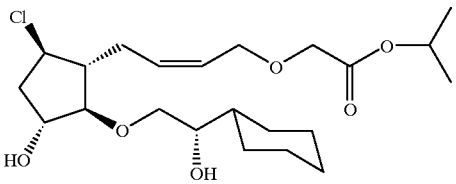

14. A compound of formula I:

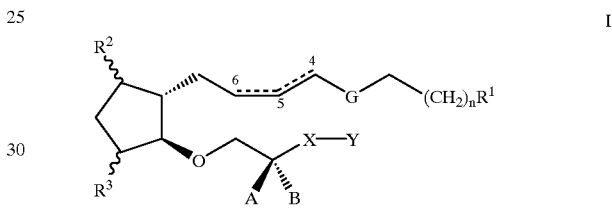

wherein:
R$^1$=CO$_2$R, CONR$^4$R$^5$, CH$_2$OR$^6$, or CH$_2$NR$^7$R$^8$; where:
  R=H or cationic salt moiety, or CO$_2$R forms a pharmaceutically acceptable ester moiety;
R$^4$, R$^5$=same or different=H or alkyl; R$^6$=H, acyl, or alkyl;
R$^7$, R$^8$=same or different=H, acyl, or alkyl; with the proviso that if one of R$^7$, R$^8$=acyl, then the other=H or alkyl;
n=0 or 2;
G=CH$_2$ or O;
R$^2$, R$^3$=same or different=OH, acyloxy, alkoxy, carbonyl, halogen, H, with the proviso that at least one of R$^2$, R$^3$=OH, acyloxy, alkoxy, or carbonyl;

----- = single or non-cumulated double bond;

one of A, B=H, the other=halo, OH, acyloxy, alkoxy;
or A—B=O(CH$_2$)$_2$O or double bonded O;
X=(CH$_2$)$_q$ or (CH$_2$)$_q$O; where q=1–6; and
Y=a phenyl ring optionally substituted with alkyl, halo, trihalomethyl, alkoxy, acyl, acyloxy, amino, alkylamino, acylamino, or hydroxy; or
X—Y=(CH$_2$)$_p$Y$^1$; where p=0–6; and

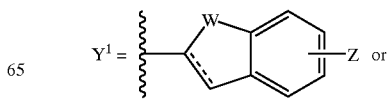

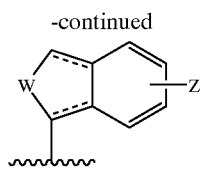

wherein:
W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and ----- = single or double bond;

or

X—Y=cyclohexyl or cyclopentyl;
with the proviso that the following compounds be excluded:

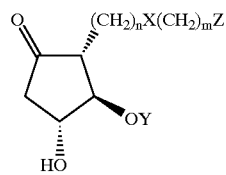

wherein:
Z=$CH_2OH$, $CONHR^1$, or $CO_2R^2$;
$R^1$=H or alkyl;
$R^2$=H, optionally substituted phenyl or naphthyl, $C_{1-6}$ alkyl, $C_{7-10}$ phenalkyl, and physiologically acceptable salts;
n=1 and m=3 or 5; or n=2 and m=2 or 4;
X=$CH_2CH_2$, or cis- or trans-CH=CH;
Y=

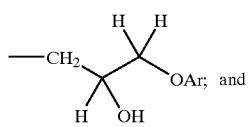

Ar=a phenyl ring, optionally substituted with alkyl, halo, trihalomethyl, or alkoxy.

15. The compound of claim 14, wherein for formula I:
$R^1$=$CO_2R$, where R=H or $CO_2R$ forms a pharmaceutically acceptable ester moiety;
n=0;
G=$CH_2$;
$R^2$=$R^3$=OH in the α configuration, or $R^2$=O (as a carbonyl) and $R^3$=OH in the α configuration or H;

----- = single or non-cumulated double bond;

one of A, B=H, the other=halo or OH;
X=$(CH_2)_2$ or $CH_2O$; and
Y=phenyl, optionally substituted with halo or trihalomethyl; or X—Y=$Y^1$; where

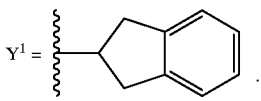

16. The compound of claim 15, having the formula:

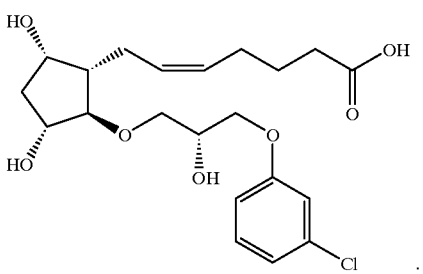

17. The compound of claim 15, having the formula:

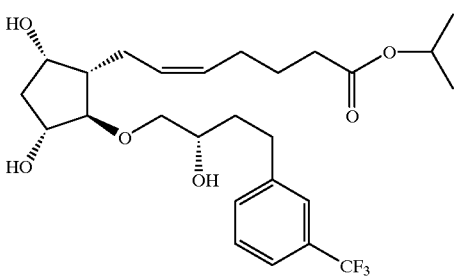

18. The compound of claim 15, having the formula:

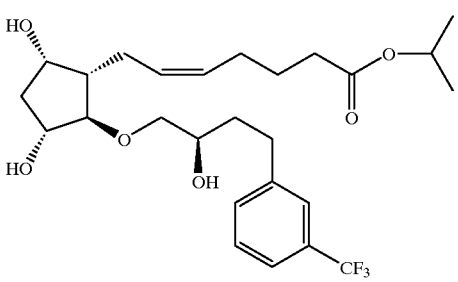

19. The compound of claim 14, wherein for formula I:
$R^1$=$CO_2R$, where R=H or alkyl $CO_2R$ forms a pharmaceutically acceptable ester moiety;
n=0;
G=O;
$R^2$=Cl in the β configuration, and $R^3$=OH in the α configuration;

----- = single or double bond, with the proviso that a single bond exists between carbons 4 and 5;
one of A, B=H, the other=halo or OH;
X—Y=cyclohexyl.

20. The compound of claim 19, having the formula:

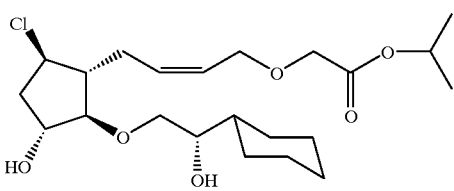

21. An ophthalmic composition for the treatment of glaucoma and ocular hypertension, comprising a compound of formula I:

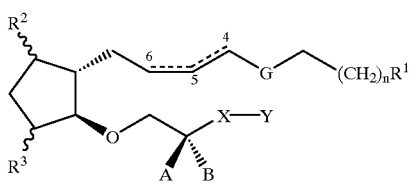

wherein:
R$^1$=CO$_2$R, CONR$^4$R$^5$, CH$_2$OR$^6$, or CH$_2$NR$^7$R$^8$; where:
R=H or cationic salt moiety, or CO$_2$R forms a pharmaceutically acceptable ester moiety;
R$^4$, R$^5$=same or different=H or alkyl; R$^6$=H, acyl, or alkyl;
R$^7$, R$^8$=same or different=H, acyl, or alkyl; with the proviso that if one of R$^7$, R$^8$=acyl, then the other=H or alkyl;
n=0 or 2;
G=CH$_2$ or O;
R$^2$, R$^3$=same or different=OH, acyloxy, alkoxy, carbonyl, halogen, H, with the proviso that at least one of R$^2$, R$^3$=OH, acyloxy, alkoxy, or carbonyl;

----- = single or non-cumulated double bond;

one of A, B=H, the other=halo, OH, acyloxy, or alkoxy; or A—B=O(CH$_2$)$_2$O or double bonded O;
X=(CH$_2$)$_q$ or (CH$_2$)$_q$O; where q=1–6; and
Y=a phenyl ring optionally substituted with alkyl, halo, trihalomethyl, alkoxy, acyl, acyloxy, amino, alkylamino, acylamino, or hydroxy; or
X—Y=(CH$_2$)$_p$Y$^1$; where p=0–6; and

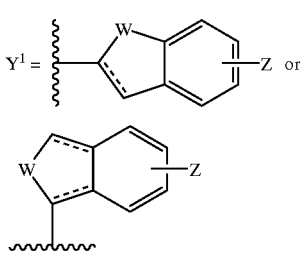

wherein:
W=CH$_2$, O, S(O)$_m$, NR$^9$, CH$_2$CH$_2$, CH=CH, CH$_2$O, CH$_2$S(O)$_m$, CH=N, or CH$_2$NR$^9$; where m=0–2, and R$^9$=H, alkyl, or acyl;
Z=H, alkyl, alkoxy, acyl, acyloxy, halo, trihalomethyl, amino, alkylamino, acylamino, or hydroxy; and ----- = single or double bond;

or

X—Y=cyclohexyl or cyclopentyl.

22. The composition of claim 21, wherein for formula I:

R$^1$=CO$_2$R, where R=H or alkyl;
n=0;
G=CH$_2$;
R$^2$=R$^3$=OH in the α configuration, or R$^2$=O (as a carbonyl) and R$^3$=OH in the α configuration or H;

----- = single or non-cumulated double bond;

one of A, B=H, the other=halo or OH;
X=(CH$_2$)$_2$ or CH$_2$O; and
Y=phenyl, optionally substituted with halo or trihalomethyl; or
X—Y=Y$^1$; where

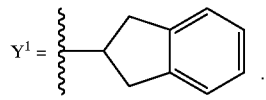

23. The composition of claim 22, having the formula:

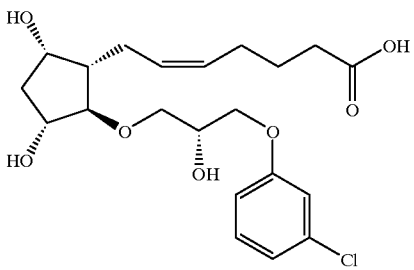

24. The composition of claim 22, having the formula:

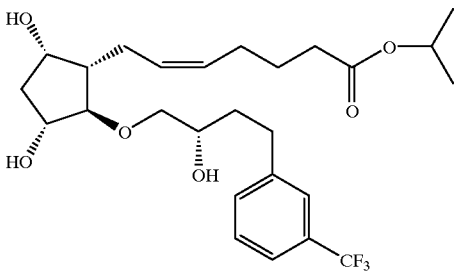

25. The composition of claim 22, having the following formula:

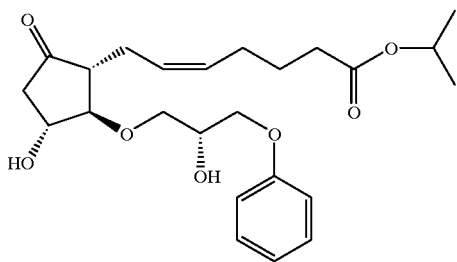

26. The composition of claim 22, having the following formula:

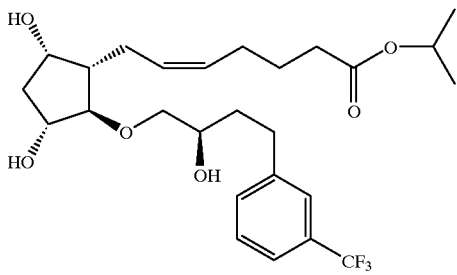

27. The composition of claim 21, wherein for formula I:

$R^1 = CO_2R$, where R=H or $CO_2R$ forms a pharmaceutically acceptable ester moiety;

n=0;

G=O;

$R^2$=Cl in the β configuration, and $R^3$=OH in the α configuration;

- - - - - = single or double bond, with the proviso that a single bond exists between carbons 4 and 5;

one of A, B=H, the other=halo or OH; and

X—Y=cyclohexyl.

28. The composition of claim 27, having the following formula:

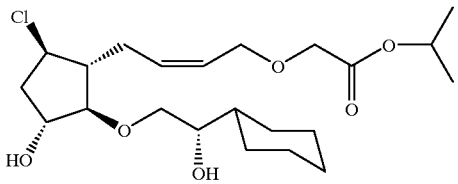

* * * * *